United States Patent [19]

Nagler et al.

[11] Patent Number: 5,998,422

[45] Date of Patent: Dec. 7, 1999

[54] QUINAZOLINONE-CONTAINING PHARMACEUTICAL COMPOSITIONS AND METHODS FOR THE USE THEREOF

[75] Inventors: Arnon Nagler; Shimon Slavin, both of Jerusalem; Israel Vlodavsky, Mevaseret Zion; Mark Pines, Rehovot, all of Israel

[73] Assignees: Agricultural Research Organization, Ministry of Agriculture, Bet Dagan; Hadasit Medical Research Services & Development Company Ltd., Kiryat Hadassah, both of Israel

[21] Appl. No.: 08/860,946

[22] PCT Filed: Dec. 21, 1995

[86] PCT No.: PCT/US95/16932

§ 371 Date: Dec. 29, 1997

§ 102(e) Date: Dec. 29, 1997

[87] PCT Pub. No.: WO96/19224

PCT Pub. Date: Jun. 27, 1996

[30] Foreign Application Priority Data

Dec. 12, 1994 [IL] Israel ........................ 112125

[51] Int. Cl.⁶ .................................. A61K 31/505
[52] U.S. Cl. ............................................ 514/259
[58] Field of Search ............................. 514/259

[56] References Cited

U.S. PATENT DOCUMENTS 4,340,596  7/1982  Schein ...................... 514/259
5,449,678  9/1995  Pines et al. ............... 514/249

*Primary Examiner*—Jerome D. Goldberg
*Attorney, Agent, or Firm*—Davidson, Davidson & Kappel, LLC

[57] ABSTRACT

The invention provides a composition for attenuating mesangial cell proliferation, comprising an amount of a compound of formula 1:

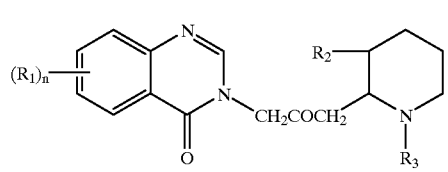

wherein: "n=1 or 2"

$R^1$ is a member of the group consisting of hydrogen, halogen, nitro, benzo, lower, alkyl, phenyl and lower alkoxy;

$R_2$ is a member of the group consisting of hydroxy, acetoxy, and lower alkoxy, and $R_3$ is a member of the group consisting of hydrogen and lower alkenoxy-carbonyl;

effective to attenuate mesangial cell proliferation and the physiologically acceptable salts thereof.

2 Claims, 6 Drawing Sheets

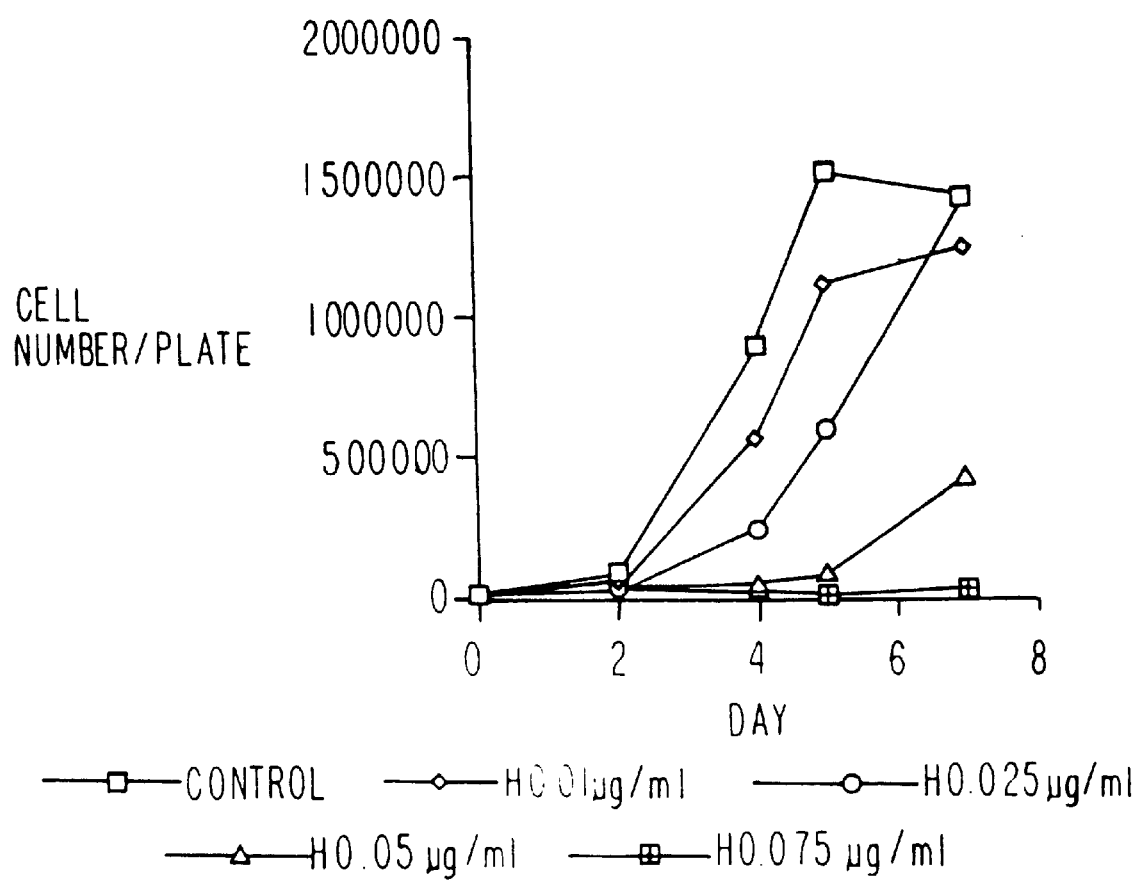

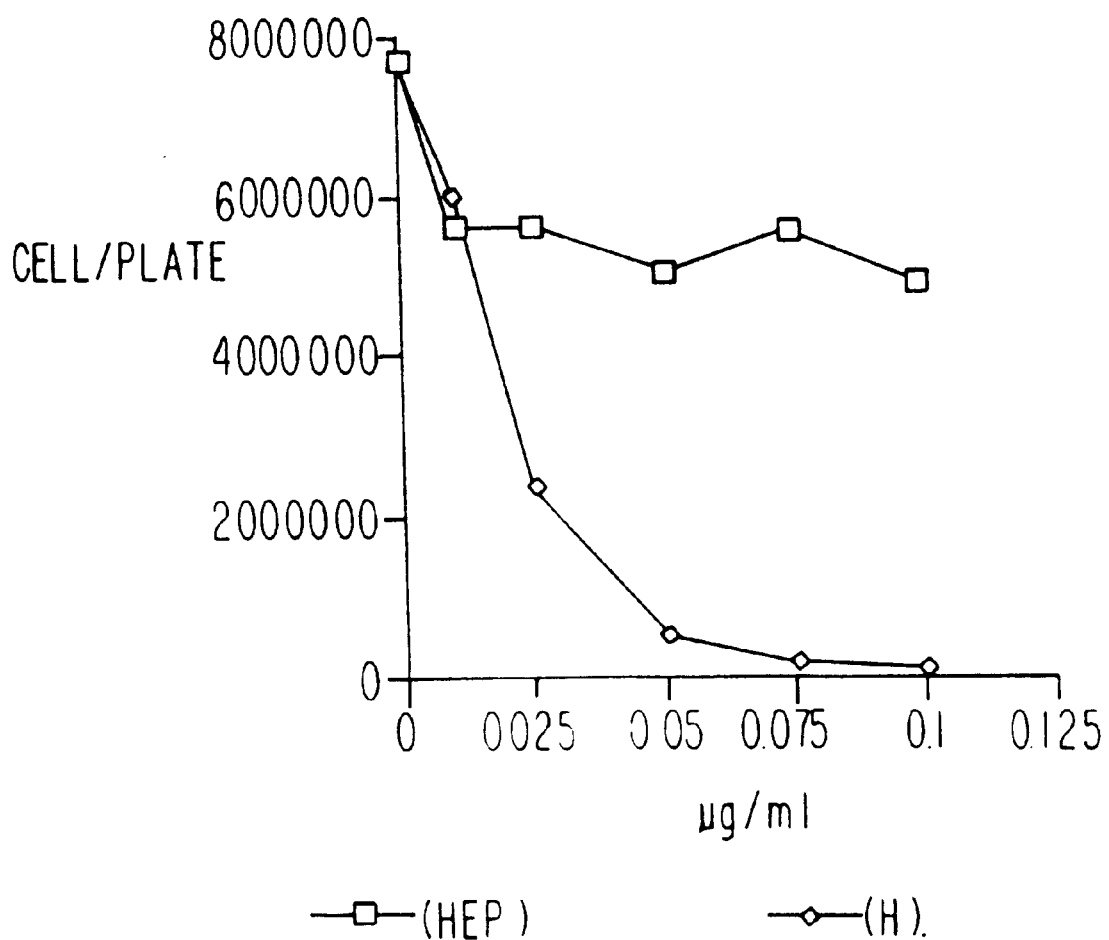

QUINAZOLINONE-CONTAINING PHARMACEUTICAL COMPOSITIONS AND METHODS FOR THE USE THEREOF

BACKGROUND OF THE INVENTION

The present invention relates to compositions containing quinazolinones. More particularly, the present invention relates to a composition for attenuating mesangial cell proliferation, comprising as active ingredient therein a quinazolinone derivative as herein defined.

In U.S. Pat. No. 3,320,124, issued in 1967, there is described and claimed a method for treating coccidiosis with quinazolinone derivatives.

Halofuginone, otherwise known as 7-bromo-6-chloro-3-[3-(3-hydroxy-2-piperidinyl)-2-oxopropyl]-4(3H)-quinazolinone, was first described and claimed in said patent by American Cyanamid Company, and was the preferred compound taught by said patent and the one commercialized from among the derivatives described and claimed therein.

Subsequently, U.S. Reissue Patent 26,833 and U.S. Pat. Nos. 4,824,847; 4,855,299; 4,861,758 and 5,215,993 all relate to the coccidiocidal properties of halofuginone, which U.S. Pat. No. 4,340,596 teaches that it can also be used for combatting theileriosis.

In 1991, one of the present inventors published an article reporting that reduced collagen synthesis was noted and identified as an important causitive factor in the skin tearing and reduced skin strength of fowl treated with halofuginone, administered in the amounts recommended for use as a coccidiostat. It was also found that, at the cellular level, halofuginone suppressed collagen synthesis by avian skin fibroblasts [I. Granot, et al., *Poult. Sci.*, Vol. 70, pp. 1559–1563 (1991)].

At that time, however, it was neither taught, recognized or suspected that halofuginone or the related quinazolinone derivatives taught in U.S. Pat. No. 3,320,124 could be effectively used for treatment of fibrotic diseases and for related cosmetic applications, and for good reason.

Clinical conditions and disorders associated with primary or secondary fibrosis, such as systemic sclerosis, graft-versus-host disease (GVHD), pulmonary and hepatic fibrosis and a large variety of autoimmune disorders, are distinguished by excessive production of connective tissue, resulting in destruction of normal tissue architecture and function. These diseases can best be interpreted in terms of perturbations in cellular functions, a major manifestation of which is excessive collagen deposition.

It is generally recognized that at present, most treatments of fibrotic diseases are ineffective and have little effect upon their inexorable pathological progression. Various attempts have been made in order to reduce collagen deposition in the extracellular space. As is known, progressive fibroproliferative diseases exhibit excessive production of connective tissues, which results in destruction of normal tissue architecture and function. The crucial role of collagen in fibrosis has prompted attempts to develop drugs that inhibit its accumulation [K. I. Kivirikko, *Annals of Medicine*, Vol. 25, pp. 113–126 (1993)].

Such drugs can act by modulating the synthesis of the procollagen polypeptide chains, or inhibit some specific post-translational events, which will lead either to reduced formation of extra-cellular collagen fibers or to an accumulation of fibers with altered properties. Only a few inhibitors of collagen synthesis are available, despite the importance of this protein in sustaining tissue integrity and its involvement in various disorders.

Cytotoxic drugs have been used in an attempt to slow collagen-producing fibroblast proliferation [J. A. Casas, et al., *Ann. Rhem. Dis.*, Vol. 46, p. 763 (1987)], among them colchicine, which slows collagen secretion into the extracellular matrix [D. Kershenobich, et al., *N. Engl. J. Med.*, Vol. 318, p. 1709 (1988)] and inhibitors of key collagen metabolism enzymes [K. Karvonen, et al., *J. Biol. Chem.*, Vol. 265, p. 8415 (1990) and C. J. Cunliffe, et al., *J. Med. Chem.*, Vol. 35, p. 2652 (1992)].

Unfortunately, none of these inhibitors are collagen-type specific. Also, there are serious concerns about toxic consequences of interfering with biosynthesis of other vital collagenous molecules, such as Clq in the classical complement pathway, acetylcholine esterase of the neuro-muscular junction endplate, conglutinin and pulmonary surfactant apoprotein.

Other drugs which can inhibit collagen synthesis, such as nifedipine and phenytoin, inhibit synthesis of other proteins as well, thereby blocking the collagen biosynthetic pathway non-specifically [T. Salo, et al., *J. Oral Pathol. Med.*, Vol. 19, p. 404 (1990)].

Collagen cross-linking inhibitors such as β-aminopropionitrile are also non-specific, although they can serve as useful antifibrotic agents. Their prolonged use causes lathritic syndrome and interferes with elastogenesis, since elastin, another fibrous connective tissue protein, is also cross-linked. In addition, the collagen cross-linking inhibitory effect is secondary, and collagen overproduction has to precede its degradation by collagenase.

In U.S. Pat. No. 5,449,678, there is described and claimed a method for the treatment of a human patient suffering from a fibrotic condition, comprising administering to the patient a composition comprising a pharmaceutically effective amount of a pharmaceutically active compound of formula I:

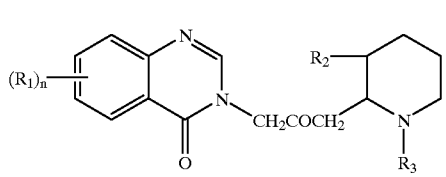

wherein "n=1 or 2"

$R_1$ is a member of the group consisting of hydrogen, halogen, nitro, benzo, lower alkyl, phenyl and lower alkoxy;

$R_2$ is a member of the group consisting of hydroxy, acetoxy, and lower alkoxy, and $R_3$ is a member of the group consisting of hydrogen and lower alkenoxy-carbonyl; effective to inhibit collagen type I. synthesis.

After further research and development, it has now been discovered that halofuginone can be used to attenuate mesangial cell proliferation. It is therefore believed that the other quinazolinone derivatives described and claimed in U.S. Pat. No. 3,320,124l, the teachings of which are incorporated herein by reference, have similar properties.

SUMMARY OF THE INVENTION

Thus, according to the present invention, there is now provided a composition for attenuating mesangial cell proliferation, comprising an amount of a compound of formula I:

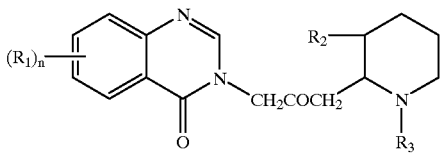

wherein: "n=1 or 2"

$R^1$ is a member of the group consisting of hydrogen, halogen, nitro, benzo, lower alkyl, phenyl and lower alkoxy;

$R_2$ is a member of the group consisting of hydroxy, acetoxy, and lower alkoxy, and $R_3$ is a member of the group consisting of hydrogen and lower alkenoxy-carbonyl; effective to attenuate mesangial cell proliferation and the physiologically acceptable salts thereof.

The invention also provides a method for the treatment of a human patient suffering from mesangial cell proliferation, comprising administering to the patient a composition comprising a pharmaceutically effective amount of a pharmaceutically active compound of formula I:

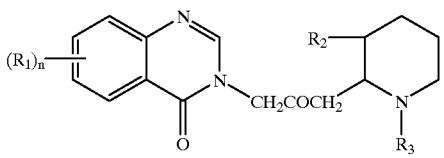

wehrein "n=1 or 2"

$R_1$ is a member of the group consisting of hydrogen, halogen, nitro, benzo, lower alkyl, phenyl and lower alkoxy;

$R_2$ is a member of the group consisting of hydroxy, acetoxy, and lower alkoxy, and $R_3$ is a member of the group consisting of hydrogen and lower alkenoxy-carbonyl; effective to attenuate mesangial cell proliferation and the physiologically acceptable salts thereof.

In preferred embodiments of the present invention, said

DETAILED DESCRIPTION OF THE INVENTION compound is halofuginone.

Figure 1:
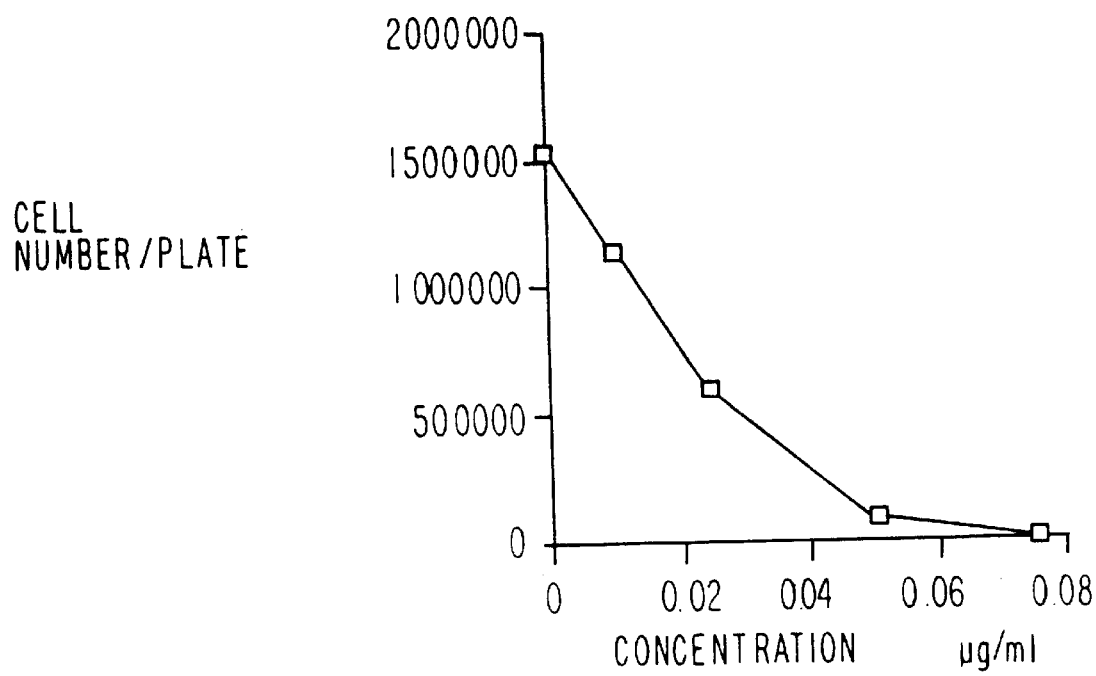

In U.S. Pat. No. 5,449,678 it is explicitly shown and demonstrated that said compounds of the present invention are effective in the treatment of fibrotic conditions such as scleroderma and graft-versus-host disease. Such a showing obviates any groundless speculation that the compound may be inactivated before producing an effect; that the compound may not reach the target area, or that other functional properties may make the compound unsuitable for in vivo use. These possibilities, however, are entirely controverted by the very fact that the identical compounds have been shown to be effective in the treatment of two specific fibrotic conditions associated with excessive collagen deposition, i.e., scleroderma and GVHD; therefore, the teachings of said U.S. Patent Application are incorporated herein by reference.

Referring now to the novel discovery of the present invention, focal and segmental glomerulosclerosis (FSGS) is the histological description of a form of golmerular injury that is usually associated with proteinuria and progressive loss of renal function [see, e.g., H. G. Rennke and P. S. Klein, "Pathogenesis and Significance of Nonprimary Focal and Segmental Glomerulosclerosis," Am. J. Kid. Dis., Vol. 13, pp. 443–46 (1989)].

Originally, FSGS was described in nephrotic patients who had died in end stage renal failure. In more recent years, FSGS has been identified as a final common pathway in the glomerulus in a number of human systemic and renal diseases. These include processes such as normal aging and diabetic nephropathy. The pathologic lesion of FSGS can result from a variety of seemingly unrelated injurious stimuli, leading through mesangial expansion and glomerulosclerosis to renal demise long after the termination of the initial injury. The lesion of FSGS is also pivotal in the animal model used most commonly to study the progression of renal disease—the renal ablation model.

The lesion of FSGS shows many similarities to the process of atherosclerosis [see, e.g., J. R. Diamond and M. J. Karnovsky, "Focal and Segmental Glomerulosclerosis: Analogies to Atherosclerosis," Kid. Int., Vol. 33, pp. 917–924 (1988)]J. In both, the participant cells are vascular endothelial cells and the underlying vascular smooth muscle cell (VSMC), or their renal counterpart: the mesangial cells. These latter cell types are closely related in terms of origin, microscopic anatomy, and histochemical characteristics. Additionally, these cells share functional properties, including angiotensin II receptors; calcium-dependent contractile response to several mediators, and a proliferative response to platelet and macrophage derived products. The progression of both renal and vascular sclerosis is affected by hypertension and vascular stress, hyper-lipedemia, and activation of the coagulation cascade, as described, inter alia, by M. Kashgarian and R. B. Sterzel, "The Pathobiology of the Mesangium," Am. J. Kid. Dis., Vol. 41, pp. 524–529 (1992).

As stated above, it has now been discovered that halofuginone is a potent inhibitor of human mesangial cell proliferation, as will be described herein further below.

As is known, the mesangium forms the axial space of the glomerulus. It consists of mesangial cells—the third type of the glomerular cell population (the others being the endothelial and epithelial cells), and of the mesangial matrix. The mesangial cell is localized in a precarious position, being in contact with the glomerular capillary lumen via the fenestrated endothelium. The mesangium is thus constantly perfused by macromolecules and filtration residues. These residues may include phlogenic immune complexes or circulating cytokines which may activate mesangial cells to proliferate and to change their secretory phenotype with respect to their production of matrix. Mesangial proliferation with expansion of the mesangial extracellular matrix either precedes or accompanies the process of glomerular sclerosis [see, e.g., A. El Nahas Meguid, "Growth Factors and Glomerular Sclerosis," Kid. Int., Vol. 41, pp. S15–S20 (1992); J. Floege, et al., "Regulation of Mesangial Cell Proliferation," Am. J. Kid. Dis., Vol. 17, pp. 673–676 (1991).]

In addition, proliferation of mesangial cells and/or mesangial matrix expansion is a cardinal feature of diseases such as lupus nephritis, IgA nephropathy, Hennoch-Schoenlein purpura, and membrano-proliferative glomerulonephritis. The capability to attenuate mesangial cell proliferation is therefore expected to prevent the progression to end stage renal disease occurring in the context of the histopathologic lesion of focal segmental FSGF. Moreover, it may be applied as a therapeutic tool in the treatment of the above-mentioned kidney diseases, which are characterized by mesangial expansion. The pathogenesis of FSGS involves abnormal proliferation of mesangial cells (MC) embedded in extracellular matrix (ECM) [see H. G. Rennke, et al., ibid.; J. R. Diamond, et al., ibid.)

Under physiological conditions, the majority of renal MCs remains in the $G_o$ phase and cell growth is controlled by a balance between endogenous growth-promoting factors and proliferation-inhibiting molecules. In response to injurious stimuli, platelets and non-platelet derived growth factors and cytokines are released and stimulate MC proliferation. Among these growth factors are platelet derived growth factor (PDGF), basic fibroblast growth factor (bFGF), and interleukin-1 (IL-1). Molecules that interfere with the growth-promoting activity of these growth factors may attenuate the progression glomerulosclerosis. Among these are species of heparin [see J. Floege, et al., "Heparin Supresses Mesangial Cell Proliferation and Matrix Expansion in Experimental Mesangioproliferative Glomerulonephritis," Kid. Int., Vol. 43, pp. 369–380 (1993); A. Wolthuis, et al., "Heparins Modulate Extracellular Matrix and Protein Synthesis in Rat Mesanglial Cells, Virchows Arch B," Cell Pathol., Vol. 63, pp. 181–189 (1993).] and, in all likelihood, heparan sulfate [see A. Schmidt, et al., "The Antiproliferative Activity of Arterial Heparan Sulfate Resides in Domains Enriched with 2-O-Sulfated Uronic Acid Residues," J. Biol. Chem., Vol. 267, pp. 19242–19247 (1992)] and other polyanionic molecules [see M. Benezra, et al., "Antiproliferative Activity to Vascular Smooth Muscle Cells and Receptor Binding of Heparin-Mimicking Polyaromatic Anionic Compounds," Arterioscler. Thromb., Vol. 14 (December 1994), in press; F. Pugliese, et al., "Regulation of Cultured Human Mesanglial Cell Growth by Ionized Macromolecules," J. Am. Soc. Nephrol., Vol. 2, pp. 595–599 (1992)].

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

The results of the experiments carried out are described below with reference to the attached figures.

Figure 2B:
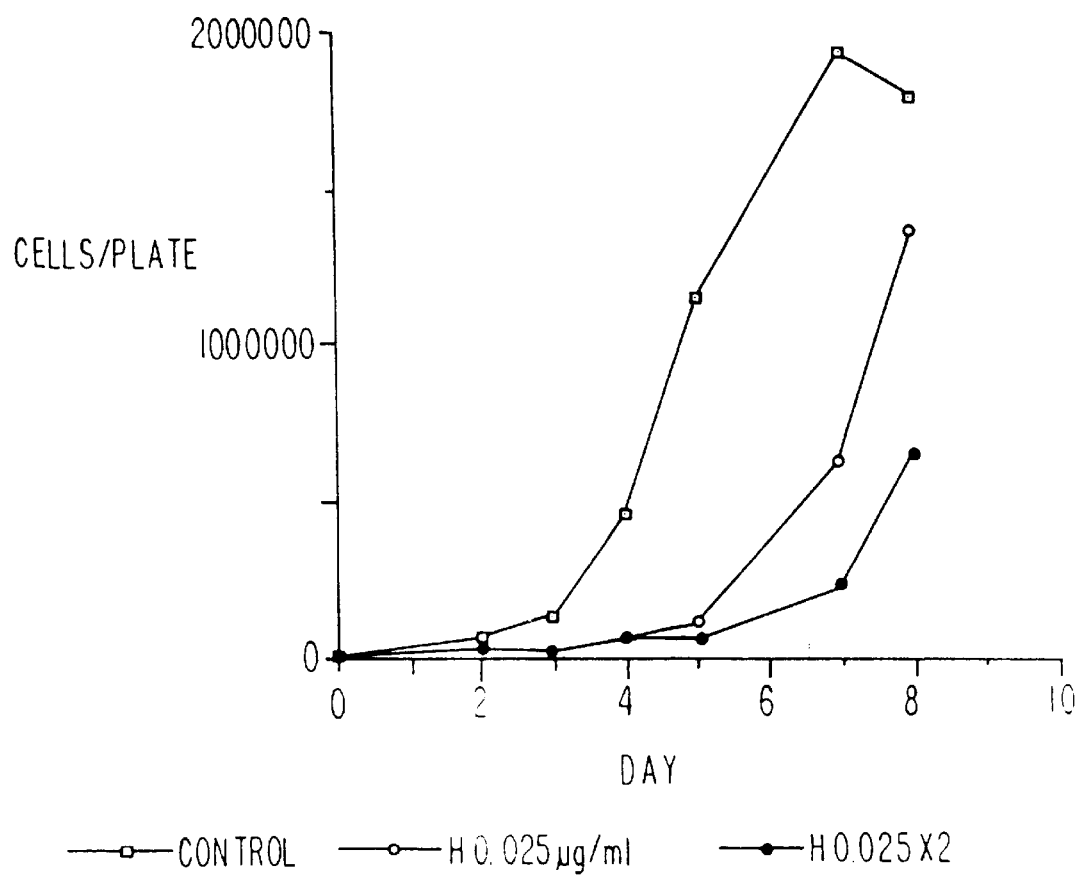
Figure 3:
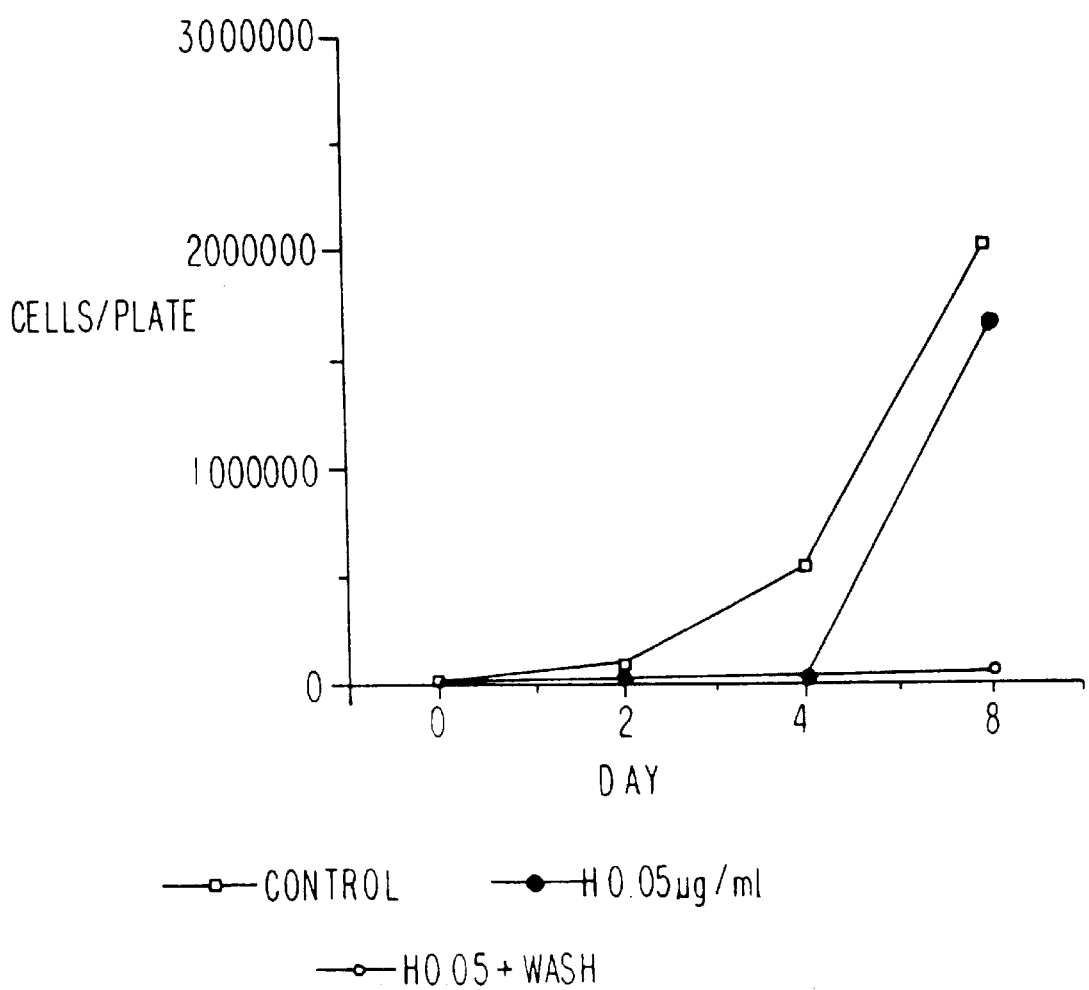
Figures 1, 4B:
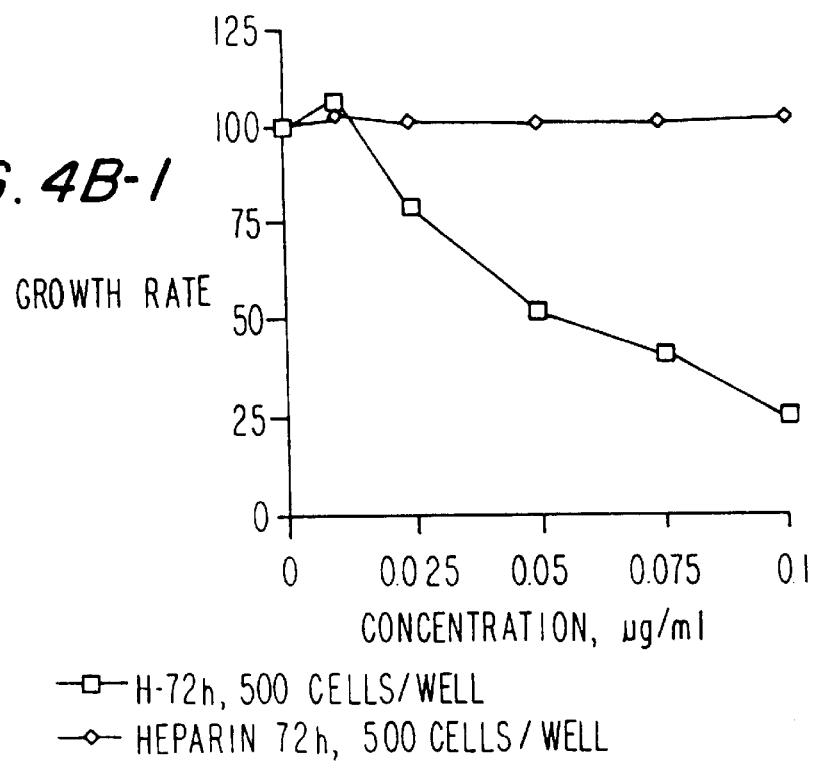
Figures 2, 4B:
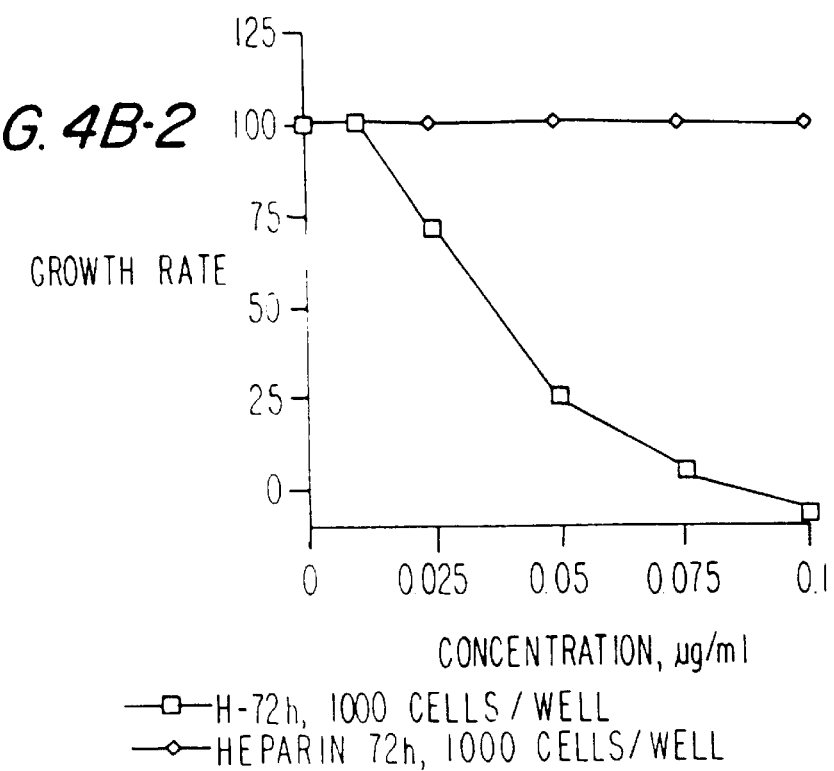

In the drawings:

FIG. 1 is a characteristic curve showing the inhibitory effect of increasing concentrations of halofuginone on mesangial cell proliferation;

FIG. 2 is a characteristic curve showing the antiproliferative effect of halofuginone toward mesanglial cells as a function of concentration (10–75 ng/ml) and days in culture, FIG. 2A showing the effect of halofuginone added on day 1, and FIG. 2B showing the effect of halofuginone added both on day 1 and on day 4;

FIG. 3 is a characteristic curve showing reversion of the antiproliferative effect of 0.05 μg/ml halofuginone on glomerular mesangial cells; and FIG. 4 is a characteristic curve comparing the effect of increasing concentrations of halofuginone and heparin on the cell number (FIG. 4A) and the growth rate (FIG. 4B) of glomerular mesangial cells.

EXAMPLES

I. Experimental procedures

Cells

Primary cultures of mesangial cells were obtained from isolated rat glomeruli, as previously described (see A. Amore, et al., "Functional Consequences of the Binding of Gliadin to Cultured Rat Mesangial Cells: Bridging Immunoglobin A to Cells and Modulation of Eicosanoid Synthesis and Altered Cytokine Production," Am. J. Kid. Dis.,Vol. 23, pp. 290–301 (1994)].

Briefly, renal cortices from rat kidneys were dissected from the medulla and capsule, minced to a paste, gently pressed through a 106-mm. steel sieve, and finally suspended in PBS. Glomeruli were isolated from this suspension by serial sieving on nylon sieves. Washed glomeruli were resuspended in RPMI and digested with type IV collagenase for 5 min. at 37° C. to remove epithelial cells. After resuspension, the glomeruli were plated onto plastic culture dishes. Cells were subcultured at near confluence. Experiments are performed on cells after the third to fourth subculture.

Glomerular mesangial cell line (SV40 MES 13) was obtained from the ATCC. The culture medium was composed of a 3:1 mixture of Dulbecco's modified Eagle's medium and Ham's F-12 medium, supplemented with 5% fetal bovine serum, and 14 mM HEPES.

The SV40 MES 13 cell line was established in 1986 from a 7- to 10-week old C57B1/6J X SJL/J mouse transgenic for the early region of simian virus 40 (SV40). Glomerular mesangial cells were isolated, trypsinized, and cloned. These mesangial cells display prominent cytoskeletal staining for actin with abundant parallel fibrils throughout the cytoplasm and contract in the presence of $10^{-6}$M angiotensin II. They have a reported doubling time of 26 h in 5% fetal bovine serum and are able to form colonies in soft agar. The cells appear to have an infinite life span in culture and stain for large T antigen. The cell line is cytokeratin and factor VIII related antigen negative. Despite their transformed phenotype the SV40 MES 13 cell line maintains features of normal glomerular mesangial cells and are useful in the study of glomerular cell biology [see L. J. Striker, et al., "Glomerular Epithelial, Mesanglial and Endothelial Cell Lines from Transgenic Mice," Kid. Int., Vol. 33, pp. 677–684 (1988)].

Cell Proliferation

A. $^H$-thymidine Incorporation Cells were plated ($4\times10^4$ cells/16 mm well) in DMEM supplemented with 10% FCS. Twenty-four hours after seeding, the medium was replaced with medium containing 0.2% FCS, and 48 h later the cells were exposed to growth stimulants and $^3$H-thymidine (1 Ci/well) for an additional 24–48 h. DNA synthesis was assayed by measuring the radioactivity incorporated into trichloroacetic acid insoluble material [see M. Benezra, et al., "Thrombin-Induced Release of Active Basic Fibroblast Groth Factor-Heparan Sulfate Complexes from Subendothelial Extracellular Matrix," Blood, Vol. 81, pp. 3324–3332 (1993)].

B. Growth Rate

Cells ($1.5\times10^4$ cells/well) were seeded into 24-well culture plates and exposed to growth stimulants as described above. One to six days after seeding, the cells were fixed with 2.5% formaldehyde in PBS. The plates were immersed in a bath of 0.1M borate buffer (pH 8.5), stained (1 h, 24° C.) with methylene blue (1% in 0.1M borate buffer, pH 8.5) and washed four times in water. This procedure removed practically all non-cell-bound dye. Specific cell incorporated methylene blue was dissolved with 0.5 ml of 0.1 N HCl (1 h, 25° C.) and determined by measuring the absorbency at 620 nm[9]. Cell number determined by cell counting correlated with the spectrophotometric absorbency [see R. Glodman and Z. Bar-Shavit, "Dual Effect of Normal and Stimulated Macrophages and Their Conditioned Media on Target Cell Proliferation," *J. Natl. Cancer Inst.*, Vol. 63, pp. 1004–1016 (1979)].

The initial cell plating density was chosen to ensure a linear relationship between cell number and absorbance at the end of the experiment. In each experiment, 3 wells were fixed before adding the test compound to determine the initial average absorbance. This value was used to calculate doubling times (DT) of control and drug-treated cells, using the following equation:

$$DT = \ln 2 / \ln [OD_t / OD_c] / h]$$

wherein:

DT=doubling time in hours;

$OD_t$=optical density of a test well at the end of the experiment;

$OD_c$=optical density of a control well at the beginning of the experiment;

h=duration of incubation in hours.

The growth rate was calculated by dividing the doubling time of drug-treated cells by that of control cells [A. Horowitz, et al., "In Vitro Cytotoxicity of Liposome-Encapsulated Doxorubicin: Dependence on Liposome Composition and Drug Release," *Biochim. Biophys. Acta*, Vol. 1109, pp. 203–209 (1992)].

C. Cell Number

Cells were seeded at a density of $5 \times 10^3$ cells/well of a 24-well plate. At various times after seeding, the cells were dissociated with 0.05% trypsin, 0.01 M sodium phosphate (pH 7.4) and 0.02% EDTA (STV) and counted in a Coulter counter (Coulter Electronic Ltd.).

II. Cell Proliferation

Antiproliferative Effect of Halofuginone toward Glomerular Mesangial Cells

A. Growth Rate

Sparsely seeded ($1.5 \times 10^4$ cells/well) glomerular MC were exposed to 10% FCS in the absence and presence of increasing concentrations of halofuginone. Five days after seeding, the cells were dissociated with STV and counted. As shown in FIG. 1, 60–70% inhibition of MC proliferation was obtained at 25 ng/ml with an almost complete inhibition at 50 ng/ml. In a similar experiment, cells seeded in the absence and presence of increasing concentrations of halofuginone were dissociated with STV and counted at various days after seeding. Complete inhibition of cell proliferation was obtained at 75 ng/ml halofuginone (FIG. 2A). A more potent antiproliferative effect was observed when halofuginone was added twice, on day 1 and day 4. This effect was best demonstrated at a low concentration of the drug (FIG. 2B).

B. Reversibility

In another experiment, the MC were exposed to halofuginone for 48 h, followed by removal of the drug and subsequent growth in regular growth medium. As demonstrated in FIG. 3, removal of the drug resulted in the gain of an accelerated growth rate, similar to that of the untreated MC. Similar results were obtained when the cells were seeded at a low density (500 and 1,000 cells/well) and their growth rate in the absence and presence of halofuginone was determined following staining with methylene blue, using the equation described in experimental procedures. An almost complete inhibition of growth was obtained in the presence of 75 µg/ml halofuginone (FIG. 4). Under the same conditions, there was no effect to heparin (FIG. 4).

C. [3]H-Thymidine Incorporation

Subconfluent glomerulor MC were maintained in medium containing 10% FCS and exposed (48 h, 37° C.) to H-thymidine in the absence and presence of increasing concentrations of halofuginone. Complete inhibition of DNA synthesis was observed at 0.035 (g/ml halofuginone, while 50% inhibition was obtained at a concentration as low as 0.025 µg/ml (not shown).

D. Effect on bFGF-Induced Cell Proliferation

Quiescent, growth-arrested glomerular MC were maintained (48 h) in medium containing 0.5% FCS and were stimulated to proliferate by low concentrations of basic fibroblast growth factor (bFGF). Exposure to halofuginone (0.050 µg/ml) resulted in an almost complete inhibition of bFGF-stimulated thymidine incorporation in growth-arrested MC (not shown). This result suggests that halofuginone efficiently antagonizes the growth-promoting activity of bFGF.

E. Effect of Other Compounds

Heparin was reported to exert an antiproliferative effect on glomerular MC [see J. Floege, et al., ibid.; A. Wolthius, et al., ibid.]. In our experiments, there was little or no inhibitory effect to heparin up to a concentration of 15 µg/ml, and about 25% inhibition at 50 µg/ml heparin. Similar results were obtained, regardless of whether the cell number (FIG. 4A) or growth rate (FIG. 4B) was determined.

III. Advantages over Current Approaches

Current approaches to inhibit the proliferation of glomerular MC utilize heparin [see Floege, et al., ibid.], low Mr heparin, suramin [see Pugliese, et al., ibid.], calcium channel blockers [i.e., amlodipine; see P. J. Shultz and L. Raij, "Effect of Amlodipine on Mesanglial Cell Proliferation and Protein Synthesis," *Am. J. Hypertens.*, Vol. 5, pp. 912–914 (1992)] and inhibitors of cholesterol synthesis [see M. P. O'Donnell, et al, "Lovastatin Retards the Progression of Established Glomerular Disease in Obese Zucker Rats," *Am. J. Kid. Dis.*, Vol. 22, pp. 83–89 (1993)]. Heparin is a potent anticoagulant and its antiproliferative activity is relatively small and subjected to major variations, depending on the source and manufacturing company. Suramin is highly toxic at the effective dose, while amlodipine and lovastatin exhibit a relatively small effect in vitro and fail to alter the progressive course of renal disease in humans.

The approach of the present invention utilizes a highly potent, inexpensive and non-toxic compound, which inhibits the activity of various growth factors, including bFGF, and inhibits autocrine growth of glumerular MC. Moreover, halofuginone is a low molecular weight compound, which in all likelihood can be administered orally. The compound has been approved by the FDA for use in treating farm animals. These characteristics make halofuginone a most promising, clinically useful drug for inhibiting progression of renal disease.

The use of halofuginone as a non-toxic compound which efficiently inhibits glomerular MC proliferation is expected to provide an effective strategy for inhibiting the pathophysiology of focal segmental glomerulosclerosis and other kidney diseases where mesengial expension plays a pivotal role.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for inhibiting mesangial cell proliferation, comprising contacting an effective amount of a compound of formula I:

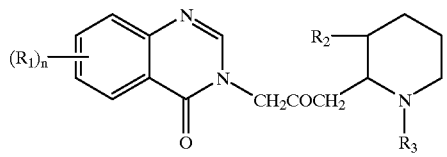

wherein:

n=1 or 2;

$R_1$ is a member of the group consisting of hydrogen, halogen nitro, benzo, lower alkyl, phenyl and lower alkoxy;

$R_2$ is a member of the group consisting of hydroxy, acetoxy, a lower akoxy, and $R_3$ is a member of the group consisting of hydrogen and lower alkenoxy-carbonyl, and physiologically acceptable salts thereof;

to proliferating mesangial cells.

2. A method according to claim 1, wherein said compound is halofuginone.